United States Patent
Beebe et al.

(10) Patent No.: US 11,029,310 B2
(45) Date of Patent: *Jun. 8, 2021

(54) DEVICE AND METHOD FOR EXTRACTING A TARGETED FRACTION FROM A SAMPLE

(71) Applicant: Wisconsin Alumni Research Foundation, Madison, WI (US)

(72) Inventors: David J. Beebe, Monona, WI (US); Scott M. Berry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 922 days.

This patent is subject to a terminal disclaimer.

(21) Appl. No.: 13/804,122

(22) Filed: Mar. 14, 2013

(65) Prior Publication Data

US 2014/0273056 A1    Sep. 18, 2014

(51) Int. Cl.
*G01N 33/551* (2006.01)
*G01N 33/543* (2006.01)
*G01N 1/34* (2006.01)
*G01N 1/40* (2006.01)
*B01L 3/00* (2006.01)

(52) U.S. Cl.
CPC ...... *G01N 33/54326* (2013.01); *B01L 3/5085* (2013.01); *B01L 3/5088* (2013.01); *G01N 1/34* (2013.01); *G01N 1/405* (2013.01); *B01L 2200/16* (2013.01); *B01L 2300/0819* (2013.01); *B01L 2300/161* (2013.01); *B01L 2400/043* (2013.01); *Y10T 436/25375* (2015.01)

(58) Field of Classification Search
USPC .......... 422/425, 503, 551; 435/287.9, 288.3; 436/526
See application file for complete search history.

(56) References Cited

U.S. PATENT DOCUMENTS

| | | | |
|---|---|---|---|
| 3,522,734 A * | 8/1970 | Curby | ........................ 73/863.21 |
| 5,279,936 A | 1/1994 | Vorpahl | |
| 5,779,907 A | 7/1998 | Yu | |
| 6,117,398 A | 9/2000 | Bienhaus et al. | |
| 7,820,454 B2 | 10/2010 | Su et al. | |

(Continued)

FOREIGN PATENT DOCUMENTS

| WO | 2006071770 | 7/2006 |
|---|---|---|
| WO | 2009/029561 | 3/2009 |

OTHER PUBLICATIONS

Bordelon et al. ("Development of a low-resource RNA extraction cassette based on surface tension valves" ACS Appl Mater Interfaces. Jun. 2011;3(6):2161-8.).*

(Continued)

*Primary Examiner* — Christopher L Chin
(74) *Attorney, Agent, or Firm* — Boyle Fredrickson, S.C.

(57) ABSTRACT

A device and a method for isolating a target from a sample are provided. The target is bound to solid phase substrate to form a target bound solid phase substrate. The device includes a first plate having a first region for receiving at least a portion of the sample. A second plate is spaced from the first plate by a distance and has a first region for receiving a reagent. A force attracts the target bound solid phase substrate toward the first region of the second plate such that the target bound solid phase substrate in the portion of the sample are drawn through the air gap and into the reagent by the force.

17 Claims, 6 Drawing Sheets

(56) References Cited

U.S. PATENT DOCUMENTS

| | | | |
|---|---|---|---|
| 8,017,340 | B2 | 9/2011 | Collier et al. |
| 8,048,633 | B2 | 11/2011 | Collier et al. |
| 8,304,188 | B2 | 11/2012 | Kelso et al. |
| 9,415,392 | B2* | 8/2016 | Ismagilov ............... C12M 1/00 435/283.1 |
| 10,590,409 | B2* | 3/2020 | Beebe ............... C12N 15/1013 |
| 2004/0224380 | A1 | 11/2004 | Chou et al. |
| 2005/0112601 | A1 | 5/2005 | Hassibi et al. |
| 2005/0208548 | A1 | 9/2005 | Block et al. |
| 2005/0227349 | A1* | 10/2005 | Kim ..................... C12N 1/02 435/287.1 |
| 2006/0024824 | A1 | 2/2006 | Woodside et al. |
| 2007/0042396 | A1 | 2/2007 | Park et al. |
| 2008/0124779 | A1 | 5/2008 | Oh et al. |
| 2008/0226500 | A1 | 9/2008 | Shikida et al. |
| 2009/0191594 | A1 | 7/2009 | Ohashi |
| 2009/0246782 | A1 | 10/2009 | Kelso et al. |
| 2010/0273142 | A1 | 10/2010 | Prins et al. |
| 2010/0291666 | A1 | 11/2010 | Collier et al. |
| 2010/0297708 | A1 | 11/2010 | Collier et al. |
| 2011/0213133 | A1* | 9/2011 | Beebe et al. ................ 530/412 |
| 2012/0094275 | A1 | 4/2012 | Rao et al. |
| 2012/0145390 | A1 | 6/2012 | Parse et al. |
| 2012/0178096 | A1 | 7/2012 | Beebe et al. |
| 2012/0190037 | A1 | 7/2012 | Durin et al. |
| 2014/0190894 | A1* | 7/2014 | Beebe ..................... G01N 1/34 210/695 |

OTHER PUBLICATIONS

"Development of an enzymatic reaction device using magnetic bead-cluster handling", Shikida et al, J. Micromech. Microeng. 16 (2006) 1875-1883.

"Controlled microfluidic interfaces", Atencia et al, Nature, vol. 437, Sep. 29, 2005, 648-655.

"Using wettability and interfacial tension to handle droplets of magnetic beads in a micro-chemical-analysis system", Shikida et al, Sensors and Actuators B 113 (2006) 563-569.

"Droplet-based gene expression analysis using a device with magnetic force-based-droplet-handling system", Okochi et al, Journal of Bioscience and Bioengineering, vol. 109, No. 2, 2010, 193-197.

"On-chip polymerase chain reaction microdevice employing a magnetic droplet-manipulation system", Tsuchiya et al, Sensors and Actuators B 130 (2008) 583-588.

"A novel Real Time micro PCR based Point-of-Care device for *Salmonella* detection in human clinical samples", Verdoy et al, Biosensors and Bioelectronics 332 (2012) 259-265.

"Forced motion of a probe particle near the colloidal glass transition", Habdas et al, Europhys. Lett., 67(3), pp. 477-583 (2004).

"Development of a Low-Resource RNA Extraction Cassette Based on Surface Tension Valves", Bordelon et al, Appl. Mater. Interfaces 2011, 3, 2161-2168.

Berry et al., "One-Step Isolation of Transitory Protein Complexes With IFast", The 16th International Conference on Miniaturized Systems for Chemistry and Life Sciences, 2012 Okinawa Japan, pp. 163-165.

EP 14765191.3, Supplementary European Search Report dated Sep. 23, 2016, 9 pages.

EP 14765191.3, EPO Communication dated Sep. 27, 2018, 4 pages.

\* cited by examiner

DEVICE AND METHOD FOR EXTRACTING A TARGETED FRACTION FROM A SAMPLE

REFERENCE TO GOVERNMENT GRANT

This invention was made with government support under CA160344 awarded by the National Institutes of Health. The government has certain rights in the invention.

FIELD OF THE INVENTION

The present invention relates generally to the preparation of biological samples, and in particular, to a device for and a method of extracting a targeted fraction from a biological sample.

BACKGROUND AND SUMMARY OF THE INVENTION

Methods for isolating DNA, RNA, and proteins from complex biological samples are some of the most crucial steps in molecular biology. However, these methods are often overlooked within the biological sample processing workflow. As the throughput of downstream analytical techniques have increased, sample preparation methods have become a limiting factor in overall throughput. Many of the most used methods for sample preparation are very time consuming and can involve many steps including substrate binding, multiple wash steps, dilutions, or other processes that can result in loss of sample or dramatic increases in assay time.

The ability to use functionalized paramagnetic particles (PMPs) to isolate analyte of interest has expanded the utility of isolation methods across a range of platforms. One of PMPs advantages is that the particles are flexible for use in many system configurations since only a magnet is required for actuation and analyte isolation. The ways to isolate an analyte of interest from a given sample can further divided into two basic methods. First, in the current primary method for using PMPs, the PMPs are held stationary while fluid is washed over the substrate to remove the background sample and any contaminants. Limitations of this popular method include the loss of the original input sample, allowing only a single effective isolation per sample, and the inefficiency of dilution-based sample preparation techniques, thereby necessitating multiple washes to effectively remove contaminants and leading to lengthy workflows. Second, recent work has demonstrated the ability to remove the PMPs from the original sample of interest using exclusion-based methods. These methods generally leverage gravitational forces or the dominance of surface tension at the microscale to position original samples and physically drag the PMPs out of the input sample along the surface of a device through some immiscible phase (e.g., air or oil) and into a second aqueous phase. These methods have been highly effective at isolating analyte with high specificity and selectivity. Further, these methods have been beneficial for their elegant workflow since isolation can be performed in a matter of seconds. Though effective, problems for these methods exist in the need for an immiscible fluid (oil) that can complicate both the fabrication and use of these techniques on larger scales and the function of 'dragging' particles along a surface which results in a friction-based loss of sample.

Therefore, it is a primary object and feature of the present invention to provide a device for and a method of extracting a targeted fraction from a biological sample.

It is a further object and feature of the present invention to provide a device for and a method of extracting a targeted fraction from a biological sample that is simple to fabricate and implement.

It is a still further object and feature of the present invention to provide a device for and a method of extracting a targeted fraction from a biological sample that reduces friction-based losses of the targeted fraction of prior devices/methods.

In accordance with the present invention, a device is provided for isolating a target from a sample. The target is bound to solid phase substrate to form target bound solid phase substrate. The device includes a first plate having a first surface and a first region for receiving at least a portion of the sample. A second plate is spaced from the first plate by a distance and has a first region for receiving a reagent. The second plate includes a first surface directed toward the first surface of the first plate. A force is provided for attracting the target bound solid phase substrate toward the first surface of the second plate. The portion of the sample received by first region of the first plate is spaced from the reagent by an air gap. The target bound solid phase substrate in the portion of the sample are drawn through the air gap and into the reagent by the force.

The first region of the first plate is defined by a portion of the first surface of the first plate wherein the first region of the first plate is hydrophilic and the first surface of the first plate external of the first region thereof is hydrophobic. In addition, the first region of the second plate is defined by a portion of the first surface of the second plate wherein the first region of the second plate is hydrophilic and the first surface of the second plate external of the first region thereof is hydrophobic. Alternatively, the first plate may include a second surface and the first region of the first plate may include a recess in the second surface and a passageway extending between the recess and the first surface of the first plate. Similarly, the first region of the second plate may include a recess in the first surface of the second plate. It is contemplated for the force to be a magnetic force and for the second plate to include a second surface. The device may also include a magnet adjacent the second surface of the second plate for generating the magnetic force.

In accordance with a further aspect of the present invention, a device is provided for isolating a target from a sample. The target is bound to solid phase substrate to form target bound solid phase substrate. The device includes a first sample receiving region for receiving at least a portion of the sample and a first reagent region for receiving a reagent. The first reagent region and the first sample region are separated by an air gap. A force is provided for drawing the target bound solid phase substrate from the at least a portion of the sample, through the air gap and into the reagent.

A first plate includes the first sample receiving region and a second plate includes the first reagent zone. The first plate includes a first surface and the first sample receiving region is defined by a portion of the first surface of the first plate. The first sample receiving region of the first plate is hydrophilic and the first surface of the first plate external of the first sample receiving region thereof is hydrophobic. The second plate includes a first surface and the first reagent region is defined by a portion of the first surface of the second plate. The first reagent region of the first plate is hydrophilic and the first surface of the second plate external of the first reagent region thereof is hydrophobic.

Alternatively, the first plate may include a second surface and the first sample receiving region of the first plate may include a recess in the second surface and a passageway extending between the recess and the first surface of the first plate. In addition, the first reagent region of the second plate may include a recess in the first surface of the second plate. In accordance with a still further aspect of the present invention, a method is provided for isolating a target from a sample. The target is bound to solid phase substrate to form target bound solid phase substrate. The method includes the steps of providing the sample at a region of a first plate and providing a reagent at a region of a second plate. The target bound solid phase substrate is drawn from the sample, through an air gap and into the reagent with a force.

The step of drawing the target bound solid phase substrate may include the step of positioning a magnetic field adjacent the second plate. The first plate includes a first surface and the region of the first plate is defined by a portion of the first surface of the first plate. The second plate also includes a first surface and the region of the second plate is defined by a portion of the first surface of the first plate. Alternatively, the first plate may include first and second surfaces. The region of the first plate includes a recess in the second surface and a passageway extending between the recess and the first surface of the first plate. Similarly, the region of the second plate may include a recess in the first surface of the second plate.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Referring to FIGS. 1-8, a device for extracting and purifying a targeted fraction, such as an analyte, from complex biological samples, including cultured cells, tissue samples and other biological materials, in accordance with the present invention is generally designated by the reference numeral 10. Device 10 includes lower plate 14, FIG. 8, having upper and lower surfaces 16 and 18, respectively. Except as hereinafter described, upper surface 16 of lower plate 14 is hydrophobic. Upper surface 16 of lower plate 14 includes first region 20 defined by edge 22 such that first region 20 has a generally circular configuration. However, other configurations are contemplated as being within the scope of the present invention. It is intended for first region 20 to retain a selected fluid thereon, as hereinafter described. As such, it is contemplated for first region 20 to be hydrophilic.

Figure 8:
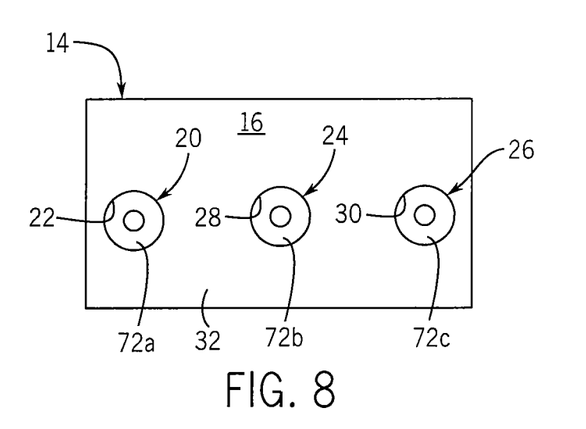
FIG. 8 is a cross-sectional view of the device of the present invention taken along line 8-8 of FIG. 1.

Upper surface 16 of lower plate 14 may further include second and third regions 24 and 26, respectively, defined by corresponding edges 28 and 30, respectively, such that second and third regions 24 and 26, respectively, have generally circular configurations. However, additional regions and/or other configurations of the regions are contemplated as being within the scope of the present invention. It is intended for second and third regions 24 and 26, respectively, to spatially retain selected fluids thereon, as hereinafter described. By way of example, it is contemplated for second and third regions 24 and 26, respectively, to be hydrophilic. Further, it is noted that the portion of upper surface 16 of lower plate 14 outside of first, second and third regions 20, 24 and 26, respectively, defines hydrophobic region 32.

Figure 7:
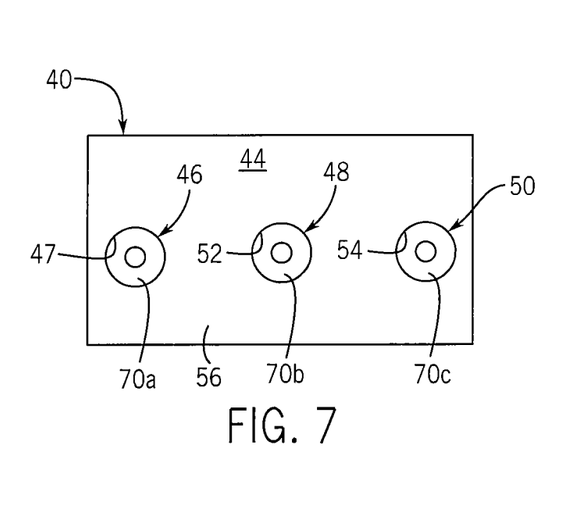
FIG. 7 is a cross-sectional view of the device of the present invention taken along line 7-7 of FIG. 1.

Device 10 further includes an upper plate 40, FIG. 7, having upper and lower surfaces 42 and 44, respectively. Except as hereinafter described, lower surface 44 of upper plate 40 is hydrophobic. Lower surface 44 of upper plate 40 includes first region 46 defined by edge 47 such that first region 46 has a generally circular configuration. However, other configurations are contemplated as being within the scope of the present invention. It is intended for first region 46 to retain a selected fluid thereon, as hereinafter described. As such, it is contemplated for first region 46 to be hydrophilic.

Lower surface 44 of upper plate 40 may further include second and third regions 48 and 50, respectively, defined by corresponding edges 52 and 54, respectively, such that second and third regions 24 and 26, respectively, have generally circular configurations. It is noted that additional regions and/or other configurations are contemplated as being within the scope of the present invention. It is intended for second and third regions 48 and 50, respectively, to retain selected fluids thereon, as hereinafter described. As such, it is contemplated for second and third regions 48 and 50, respectively, to be hydrophilic. The portion of lower surface 44 of upper plate 40 outside of first, second and third regions 47, 48 and 50, respectively, defines hydrophobic region 56.

In the depicted embodiment, a single magnet 60 is supported below lower surface 18 of lower plate 14. It is noted, however, magnet 60 may be replaced by a plurality of magnets, each of which positioned below lower surface 18 of lower plate 14 and aligned with a corresponding hydrophilic region on upper surface 16 of lower plate 14. It is contemplated for magnet 60 to be axially movable between a first position wherein magnet 60 is adjacent to lower surface 18 of lower plate 14, FIGS. 2-3, and a second position axially spaced from lower surface 18 of lower plate 14, for reasons hereinafter described, FIG. 1.

It is intended to utilize device 10 to extract a targeted fraction, such as an analyte, DNA, RNA, proteins nucleic acids, whole cells and/or the like, from biological sample 62. As is known, biological sample 62 may include non-desired material 64 such as lysate, bodily fluids, forensic samples, and/or biological contaminations. In order to prepare biological sample 62 for extraction of the fraction, an appropriate reagent is added to biological sample 62 and mixed such that the fraction binds to a solid phase substrate in the reagent to form fraction-bound solid phase substrate 66. It is contemplated for the solid phase substrate to be attracted to a corresponding force. For example, the solid phase substrate may be a paramagnetic material attracted to a corresponding magnetic field. Other non-magnetic mechanisms such as gravity, optical force, ultrasonic actuation or the like are contemplated as being within the scope of the present invention.

Once mixed with the reagent, droplets 70a-70c of biological sample 62 are deposited on first, second and third regions 46, 48 and 50, respectively, of lower surface 44 of upper plate 40, in any conventional matter such as by a micropipette or like. It is contemplated for the volumes of droplets 70a-70c to be generally equal. It can be appreciated that the hydrophilic nature of first, second and third regions 46, 48 and 50, respectively, act to pin droplets 70a-70c thereon. In addition, hydrophobic region 56 of lower surface 44 of upper plate 40 further acts to retain droplets 70a-70c on first, second and third regions 46, 48 and 50, respectively.

In addition, droplets 72a-72c of one or more desired reagents (e.g. wash, secondary antibody, etc.) are deposited on first, second and third regions 20, 24 and 26 of upper surface 16 of lower plate 14. It is contemplated for the volumes of droplets 72a-72c to be generally equal. It can be appreciated that the hydrophillic nature of first, second and third regions 20, 24 and 26, respectively, act to pin droplets 72a-72c thereon. In addition, the hydrophobic region 32 of upper surface 16 of lower plate 14 further acts to retain droplets 72a-72c on first, second and third regions 20, 24 and 26, respectively.

After depositing droplets 72a-72c on first, second and third regions 20, 24 and 26, respectively, of lower plate 14, upper plate 40 is positioned such that first, second and third regions 46, 48 and 50, respectively, of lower surface 44 of upper plate 40 are in registry with first, second and third regions 20, 24 and 26, respectively, of lower plate 14 such that droplets 70a-70c are in registry with and spaced from droplets 72a-72c by air gaps 74a-74c, respectively. With upper plate 40 positioned, as heretofore described, magnet 60 is positioned adjacent lower surface 18 of lower plate 14 such that magnet 60 magnetically attracts fraction-bound solid phase substrate 66 in droplets 70a-70c and draws fraction-bound solid phase substrate 66 toward upper surface 16 of lower plate 14, FIG. 2. More specifically, the magnetic force generated by magnet 60 draws fraction-bound solid phase substrate 66 from droplets 70a-70c, through air gaps 74a-74c, respectively, and into droplets 72-72a, respectively, on first, second and third regions 20, 24 and 26, respectively, of upper surface 16 of lower plate 14, FIG. 3. Any undesired (or unbound) material in droplets 70a-70c is retained therein by surface tension. Thereafter, magnet 60 may be moved to a location spaced from lower plate 14 such that the magnetic force generated thereby no longer acts on fraction-bound solid phase substrate 66 in droplets 72a-72c, thereby freeing fraction-bound solid phase substrate 66 within droplets 72a-72c.

Figure 1:
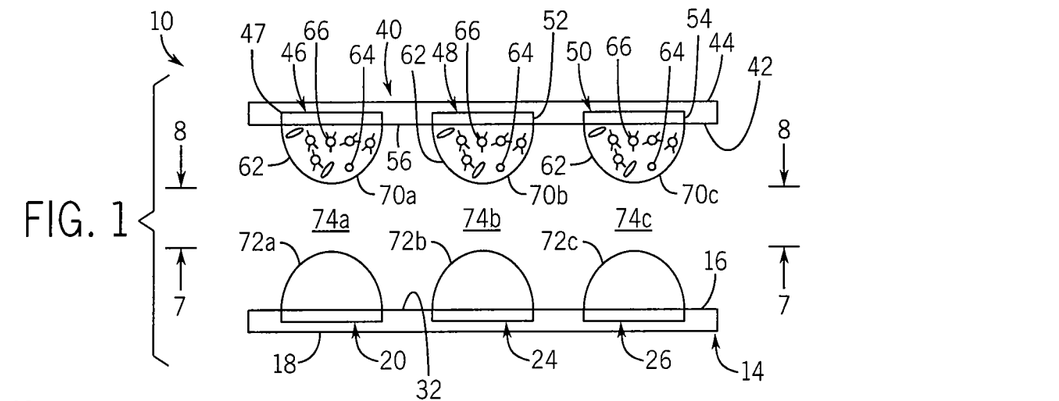
FIG. 1 is a cross-sectional view of a device in accordance with the present invention in an initial configuration.
Figure 2:
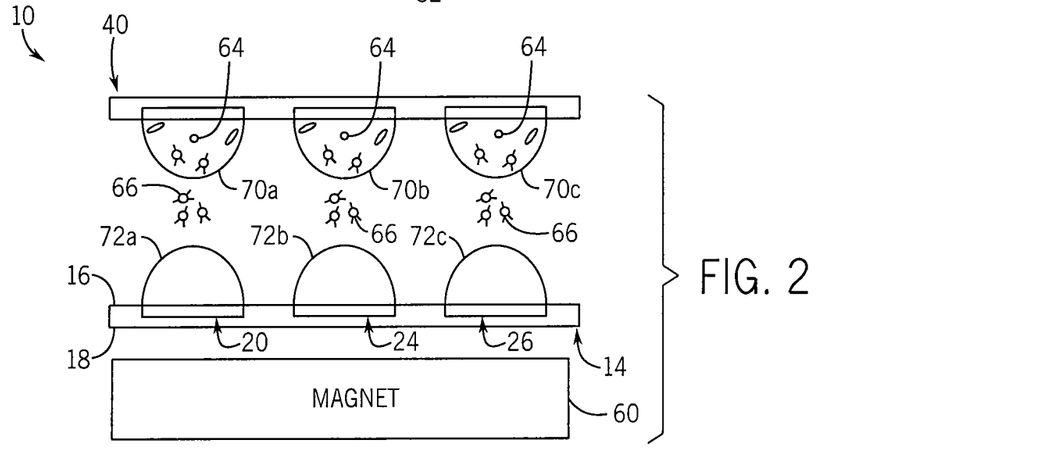
FIG. 2 is a cross-sectional view of the device of the present invention in a second configuration.
Figure 3:
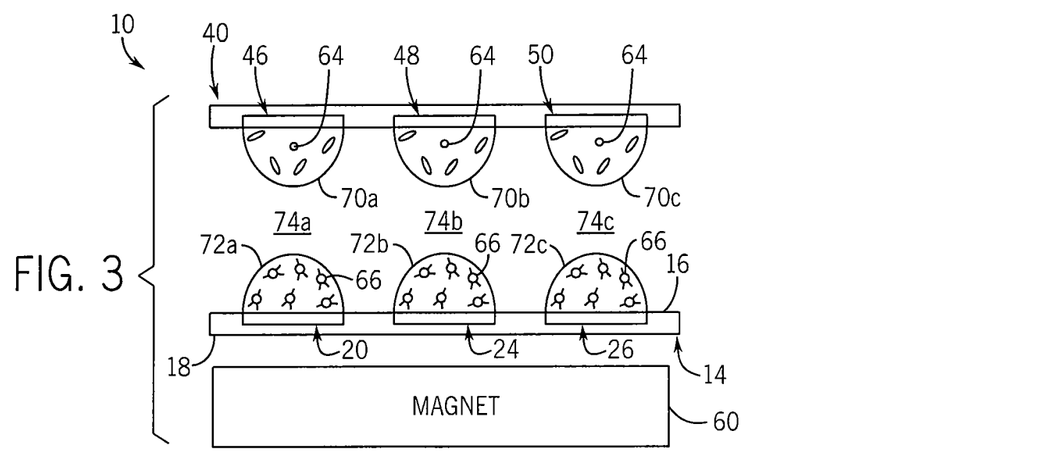
FIG. 3 is a cross-sectional view of the device of the present invention in a third configuration.
Figure 4:
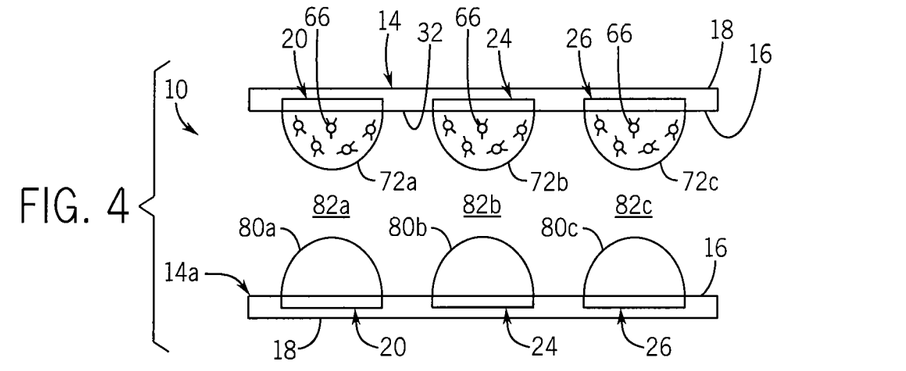
FIG. 4 is a cross-sectional view of the device of the present invention in a fourth configuration.
Figure 5:
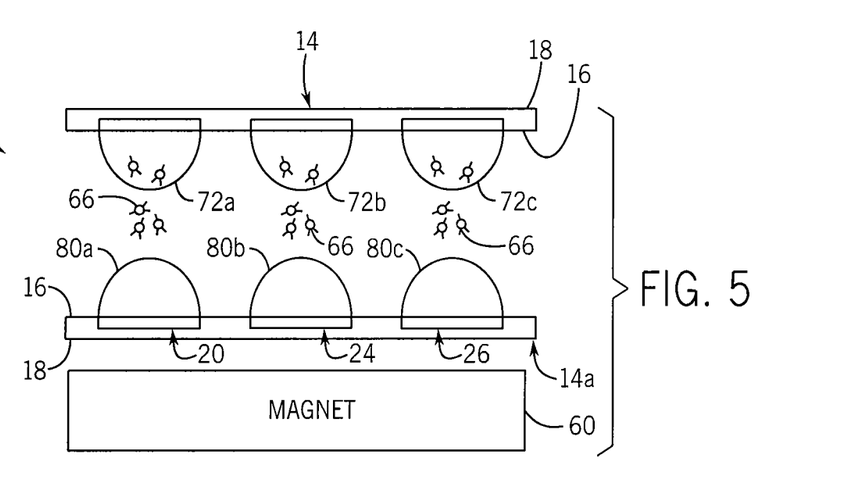
FIG. 5 is an isometric view of a device of the present invention in a fifth configuration.
Figure 6:
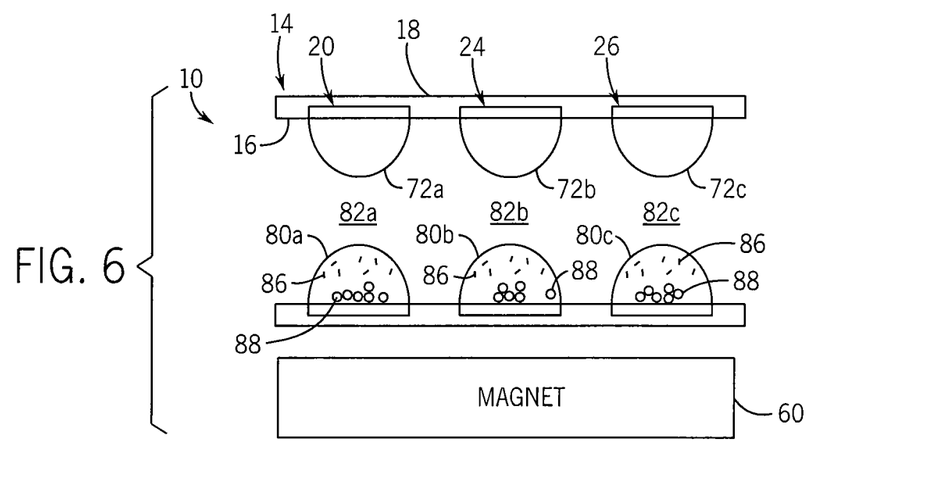
FIG. 6 is a cross-sectional view of the device of the present invention in a sixth configuration.

Referring to FIGS. 4-6, lower plate 40 (and hence, droplets 72a-72c) may be repositioned so as to allow for further processing of fraction-bound solid phase substrate 66 in droplets 72-72a. By way of example, lower plate 40 may be repositioned such that upper surface 16 of lower plate 14 may be directed downwardly toward upper surface 16 of a second lower plate 14a. Second lower plate 14a is identical in structure to lower plate 14 such that the description heretofore of lower plate 14 is understood to describe second lower plate 14a as if fully herein.

It is contemplated to provide droplets 80a-80c of one or more desired reagents (e.g. wash, secondary antibody, etc.) on first, second and third regions 20, 24 and 26 of upper surface 16 of second lower plate 14a. It is contemplated for the volumes of droplets 80a-80c to be generally equal. It can be appreciated that the hydrophilic nature of first, second and third regions 20, 24 and 26, respectively, of upper surface 16 of second lower plate 14a act to pin droplets 80a-80c thereon. In addition, the hydrophobic region 32 of upper surface 16 of second lower plate 14a further acts to retain droplets 80a-80c on first, second and third regions 20, 24 and 26, respectively, of upper surface 16 of second lower plate 14a.

As described, first, second and third regions 20, 24 and 26, respectively, of second lower plate 14a are in registry with first, second and third regions 20, 24 and 26, respectively, of lower plate 14 such that droplets 80a-80c are in registry with and spaced from droplets 72a-72c by air gaps 82a-82c, respectively. With lower plate 14 and second lower plate 14a positioned as described, magnet 60 is positioned adjacent lower surface 18 of second lower plate 14a such that magnet 60 magnetically attracts fraction-bound solid phase substrate 66 in droplets 72a-72c and draws fraction-bound solid phase substrate 66 toward upper surface 16 of second lower plate 14a, FIG. 5. More specifically, the magnetic force generated by magnet 60 draws fraction-bound solid phase substrate 66 from droplets 72a-72c, through air gaps 82a-82c, respectively, and into droplets 80a-80c, respectively, on first, second and third regions 20, 24 and 26, respectively, of upper surface 16 of second lower plate 14a, FIG. 6. Any undesired (or unbound) material in droplets 72a-72c is retained therein by surface tension. Thereafter, magnet 60 may be moved to a location spaced from second lower plate 14a such that the magnetic force generated thereby no longer acts on fraction-bound solid phase substrate 66 in droplets 80a-80c, thereby freeing fraction-bound solid phase substrate 66 within droplets 80a-80c. Droplets 80a-80c, and hence fraction-bound solid phase substrate 66 therein, are available for further processing, e.g. droplets 80a-80c may be formed from elusion buffers which disassociate target or fraction 86 from solid phase substrate 88.

Figure 9:
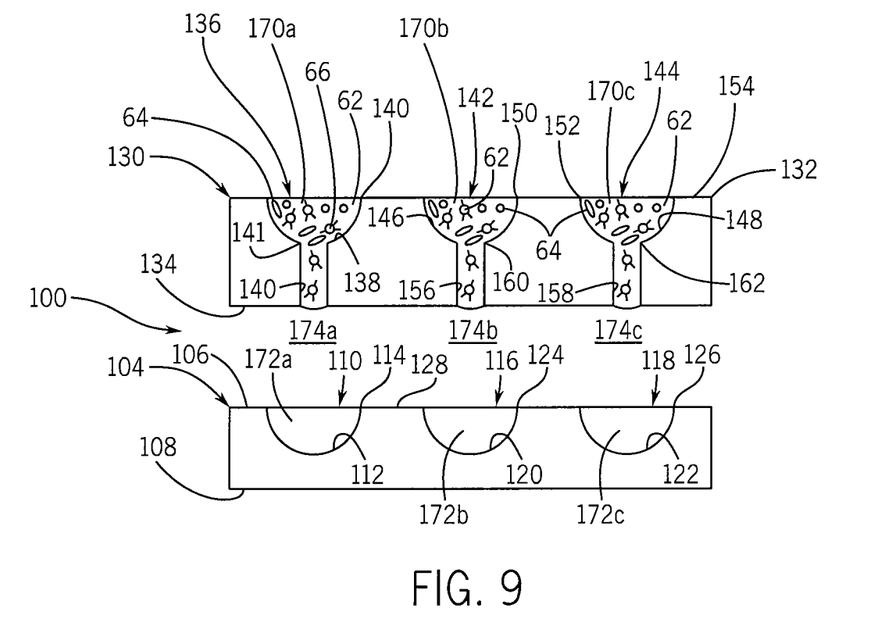
FIG. 9 is a cross-sectional view of an alternate embodiment of a device in accordance with the present invention in an initial configuration.
Figure 10:
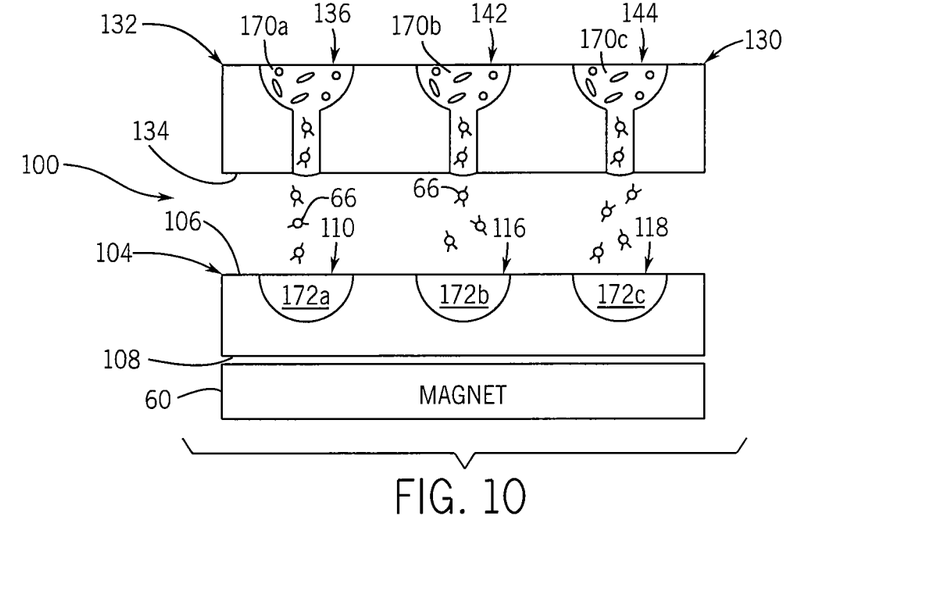
FIG. 10 is a cross-sectional view of the device of FIG. 9 in a second configuration.
Figure 11:
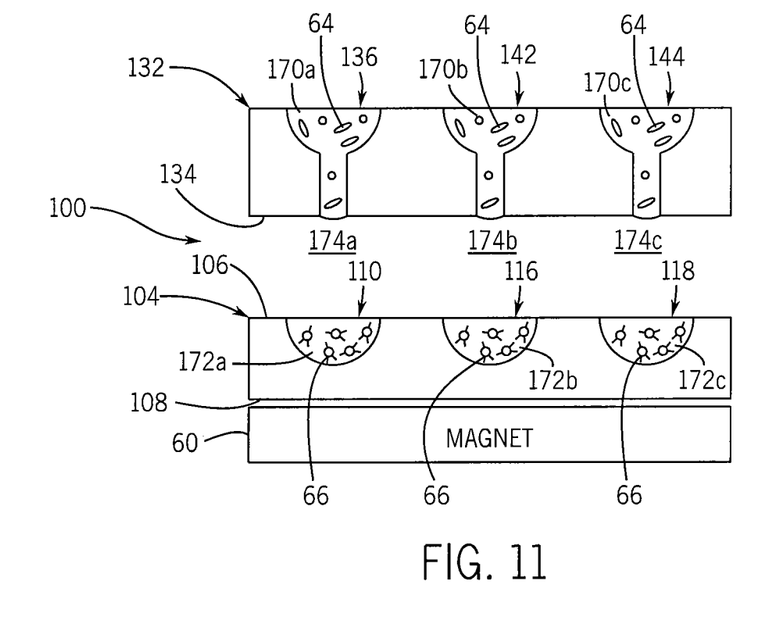
FIG. 11 is a cross-sectional view of the device of FIG. 10 in a third configuration.

Referring to FIGS. 9-11, an alternate embodiment of a device for extracting and purifying a targeted fraction, such as an analyte, from complex biological samples, including cultured cells, tissue samples and other biological materials, in accordance with the present invention is generally designated by the reference numeral 100. Device 100 includes lower plate 104 having upper and lower surfaces 106 and 108, respectively. Except as hereinafter described, upper surface 106 of lower plate 104 is hydrophobic. Upper surface 106 of lower plate 104 includes first recess 110 formed therein. In the depicted embodiment, first recess 110 is defined by concave recessed surface 112 intersecting upper surface 106 at edge 114. Edge 114 has a generally circular configuration. However, it is noted that first recess 110 may have other configurations without deviating from the scope of the present invention. It is intended for first recess 110 to retain a selected fluid therein, as hereinafter described. As such, it is contemplated for recessed surface 112 to be hydrophilic.

Upper surface 106 of lower plate 104 may further include second and third recesses 116 and 118, respectively. Second and third recesses 116 and 118, respectively, are defined by concave recessed surfaces 120 and 122, respectively, intersecting upper surface 106 at edges 124 and 126, respectively. Edges 124 and 126 have generally circular configurations. However, it is noted that second and third recesses 116 and 118, respectively, may have other configurations without deviating from the scope of the present invention. It is intended for second and third recesses 116 and 118, respectively, to retain selected fluids therein, as hereinafter described. As such, it is contemplated for recessed surfaces 120 and 122, respectively, to be hydrophilic. Further, the portion of upper surface 106 of lower plate 104 outside of first, second and third recesses 110, 116 and 118, respectively, defines hydrophobic region 128.

Device 100 further includes an upper plate 130 having upper and lower surfaces 132 and 134, respectively. Except as hereinafter described, upper and lower surfaces 132 and 134, respectively of upper plate 130 are hydrophobic. Upper surface 132 of upper plate 130 includes first recess 136 formed therein. In the depicted embodiment, first recess 136 is defined by concave recessed surface 138 intersecting upper surface 132 at edge 140. Edge 140 has a generally circular configuration. However, it is noted that first recess 136 may have other configurations without deviating from the scope of the present invention. It is intended for first recess 136 to retain a selected fluid therein, as hereinafter described. As such, it is contemplated for recessed surface 138 to be hydrophilic. Passageway 140 extends between nadir 141 of recessed surface 138 and lower surface 134 of upper plate 130. It is intended for the diameter of passageway 140 to be of sufficient dimension so as to allow fraction-bound solid phase substrate 66 to pass therethrough, for reasons hereinafter described. It is understood that length of passageway 140 may vary without deviating from the scope of the present invention. By way of example, it is contemplated for passageway 140 to take the form of an opening communicating with both first recess 136 and lower surface 134 of upper plate 130.

Upper surface 132 of upper plate 130 may further include second and third recesses 142 and 144, respectively. Second and third recesses 142 and 144, respectively, are defined by concave recessed surfaces 146 and 148, respectively, intersecting upper surface 132 at edges 150 and 152, respectively. Edges 150 and 152 have generally circular configurations. However, it is noted that second and third recesses 142 and 144, respectively, may have other configurations without deviating from the scope of the present invention. It is intended for second and third recesses 142 and 144, respectively, to retain selected fluids therein, as hereinafter described. As such, it is contemplated for recessed surfaces 146 and 148, respectively, to be hydrophilic and for the portion of upper surface 132 of upper plate 130 outside of first, second and third recesses 136, 142 and 144, respectively, to define hydrophobic region 154. Passageways 156 and 158 extend between corresponding nadirs 160 and 162 of recessed surfaces 146 and 148, respectively, and lower surface 134 of upper plate 130. It is intended for the diameters of passageways 156 and 158 to be of sufficient dimensions so as to allow fraction-bound solid phase substrate 66 to pass therethrough, for reasons hereinafter described. It is further understood that length of passageways 156 and 158 may vary without deviating from the scope of the present invention. By way of example, it is contemplated for passageways 156 and 158 to take the form of openings communicating with second and third recesses 142 and 144, respectively, and lower surface 134 of upper plate 130.

In operation, droplets 170a-170c of biological sample 62 are deposited in first, second and third recesses 136, 142 and 144, respectively, in upper surface 132 of upper plate 130 in any conventional matter such that passageways 140, 156 and 158 are filled with biological sample 62. It can be appreciated that the hydrophilic nature of first, second and third recesses 136, 142 and 144, act to maintain droplets 170a-170c therein. In addition, the hydrophobic nature of lower surface 134 of upper plate 130 along with the surface tension of the biological sample at the outputs of passageways 140, 156 and 158 further act to retain the portions of biological sample 62 within passageways 140, 156 and 158, respectively.

In addition, droplets 172a-172c of desired reagents (e.g. wash, secondary antibody, etc.) are deposited in first, second and third recesses 110, 116 and 118, respectively, in upper surface 106 of lower plate 104. It is contemplated for the volumes of droplets 172a-172c to be generally equal. It can be appreciated that the hydrophilic nature of first, second and third recesses 110, 116 and 118, respectively, act to retain droplets 172a-172c therein. In addition, the hydrophobic nature of upper surface 106 of lower plate 104 further acts to retain droplets 172a-172c in first, second and third recesses 110, 116 and 118, respectively.

After depositing droplets 172a-172c in first, second and third recesses 110, 116 and 118, respectively, of lower plate 104, upper plate 130 is positioned such that passageways 140, 156 and 158 of upper plate 130 are in registry with first, second and third recesses 110, 116 and 118, respectively, of lower plate 104. As a result, droplets 170a-170c are in registry with and spaced from droplets 172a-172c by air gaps 174a-174c, respectively. With upper plate 130 positioned, as heretofore described, magnet 60 is positioned adjacent lower surface 108 of lower plate 104 such that magnet 60 magnetically attracts fraction-bound solid phase substrate 66 in droplets 170a-170c and draws fraction-bound solid phase substrate 66 toward upper surface 106 of lower plate 104, FIG. 10. More specifically, the magnetic force generated by magnet 60 draws fraction-bound solid phase substrate 66 from droplets 170a-170c, through passageways 140, 156 and 158 and air gaps 74a-74c, respectively, and into droplets 172-172a, respectively, in first, second and third recesses 110, 116 and 118, respectively, of lower plate 104, FIG. 11. Any undesired (or unbound) material in droplets 170a-170c is retained therein by surface tension. Magnet 60 may be moved to a location spaced from lower plate 104 such that the magnetic force generated thereby no longer acts on fraction-bound solid phase substrate 66 in droplets 172a-172c. As such, fraction-bound solid phase substrate 66 in droplets 172a-172c are available for further processing.

Figure 12:
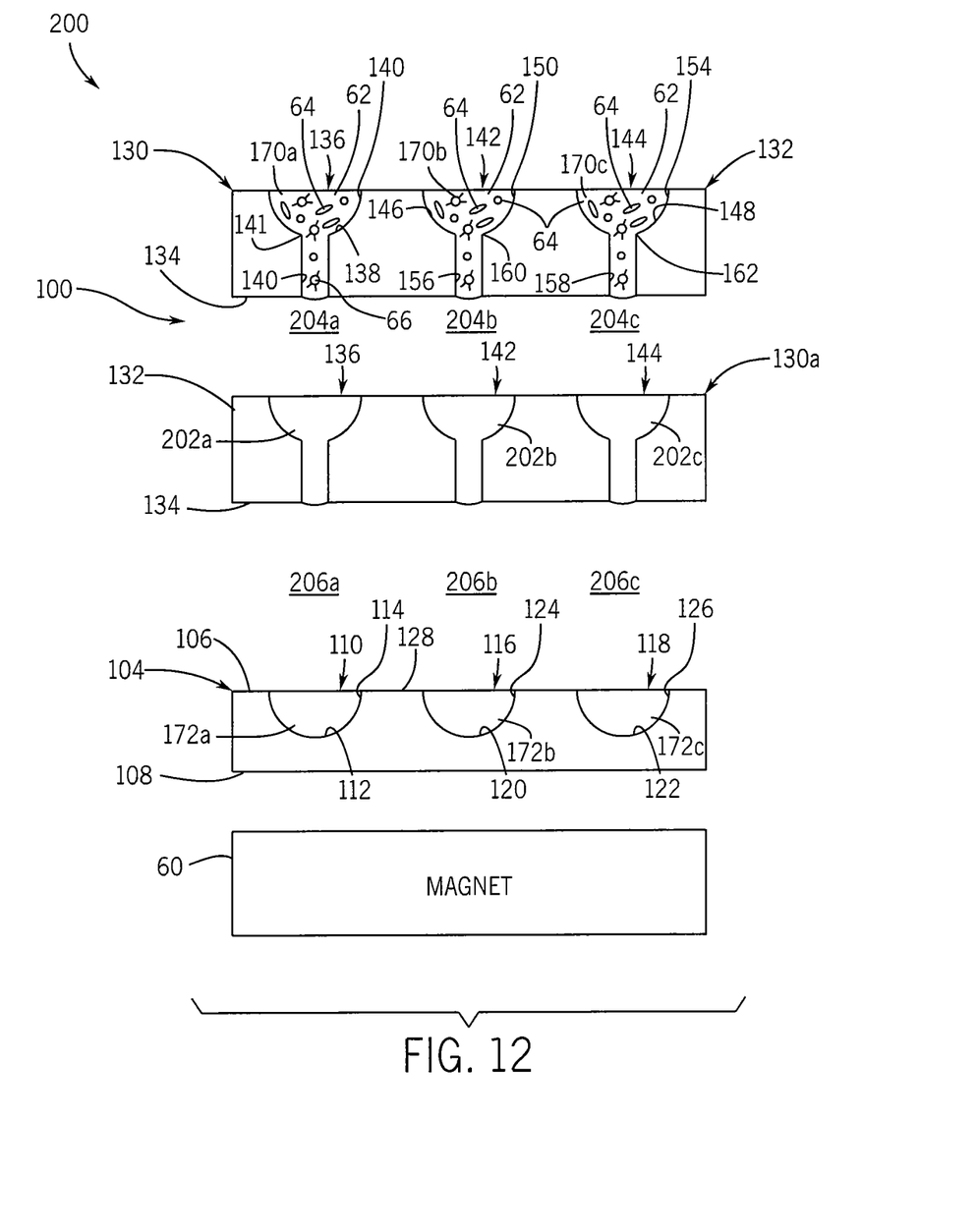
FIG. 12 is a cross-sectional view of a still further embodiment of a device in accordance with the present invention in an initial configuration.

Referring to FIG. 12, a still further embodiment of a device for extracting and purifying a targeted fraction, such as an analyte, from complex biological samples, including cultured cells, tissue samples and other biological materials, in accordance with the present invention is generally designated by the reference numeral 200. Device 200 includes upper plate 130 and lower plate 104, as heretofore described. It is contemplated to provided one or more additional upper plates, e.g. upper plate 130a, between upper plate 130 and lower plate 104, as hereinafter described. Upper plate 130a is identical in structure to upper plate 130. As such, the previous description of upper plate 130 is understood to describe upper plate 130a, as if fully described herein.

In operation, droplets 170a-170c of biological sample 62 are deposited in first, second and third recesses 136, 142 and 144, respectively, in upper surface 132 of upper plate 130 in any conventional matter such that passageways 140, 156 and 158 are filled with biological sample 62. In addition, droplets 202a-202c of desired reagents (e.g. wash, secondary antibody, etc.) are deposited in first, second and third recesses 136, 142 and 144, respectively, in upper surface 132 of upper plate 130a in any conventional matter such that passageways 140, 156 and 158 of upper plate 130a are filled therewith. Similarly, droplets 172a-172c of desired reagents (e.g. wash, secondary antibody, etc.) are deposited in first, second and third recesses 110, 116 and 118, respectively, in upper surface 106 of lower plate 104. As described, droplets 170a-170c are in registry with and spaced from droplets 202a-202c by air gaps 204a-204c, respectively, and droplets 202a-202c are in registry with and spaced from droplets 172a-172c by air gaps 206a-206c, respectively.

Magnet 60 is positioned adjacent lower surface 108 of lower plate 104 such that magnet 60 magnetically attracts fraction-bound solid phase substrate 66 in droplets 170a-170c and draws fraction-bound solid phase substrate 66 toward upper surface 106 of lower plate 104. More specifically, the magnetic force generated by magnet 60 draws fraction-bound solid phase substrate 66 from droplets 170a-170c, through passageways 140, 156 and 158 and air gaps 204a-204c, respectively, and into droplets 202a-202c, respectively, in first, second and third recesses 136, 142 and 144, respectively, in upper surface 132 of upper plate 130a wherein the reagent(s) therein are free to act on the fraction-bound solid phase substrate 66. Any undesired (or unbound) material in droplets 170a-170c is retained therein by surface tension. Thereafter, the magnetic force generated by magnet 60 draws fraction-bound solid phase substrate 66 from droplets 202a-202c, through passageways 140, 156 and 158 in upper plate 130a and air gaps 206a-206c, respectively, and into droplets 172-172a, respectively, in first, second and third recesses 110, 116 and 118, respectively, of lower plate 104. Magnet 60 may them be moved to a location spaced from lower plate 104 such that the magnetic force generated thereby no longer acts on fraction-bound solid phase substrate 66 in droplets 172a-172c. As such, fraction-bound solid phase substrate 66 in droplets 172a-172c are available for further processing.

It can be appreciated that the above descriptions of devices are merely exemplary of the present invention. Various modes of carrying out the invention are contemplated as being within the scope of the following claims particularly pointing out and distinctly claiming the subject matter, which is regarded as the invention.

We claim:

1. A device for isolating a target from a sample, the sample including the target bound to solid phase substrate to form target bound solid phase substrate, comprising:
    a first plate lying in a first plane and having a first surface, the first surface including a first region for receiving at least a portion of the sample;
    a second plate lying in a second plane which is generally parallel to and spaced from the first plate along an axis generally perpendicular to the first and second planes by a distance, the second plate having a first surface directed toward the first surface of the first plate and including a first region for receiving a reagent; and
    a magnetic force generator positionable adjacent the second plate, the magnetic force generator generating a magnetic force which draws the target bound solid phase substrate away from the first surface of the first plate toward the first surface of the second plate in a direction generally parallel to the axis when the portion of the sample is received on the first region of the first plate;

wherein:
    when the portion of the sample is received on the first region of the first plate and when the reagent is received on the first region of the second plate, the distance between the first plate and the second plate being sufficient:
        to provide an air gap between the portion of the sample received by first region of the first plate and the reagent received by the first region of the second plate; and
        for the target bound solid phase substrate in the portion of the sample to be drawn through the air gap and into the reagent by the magnetic force generated by the magnetic force generator.

2. The device of claim 1 wherein the first region of the first plate is defined by a portion of the first surface of the first plate.

3. The device of claim 2 wherein the first region of the first plate is hydrophilic.

4. The device of claim 2 wherein the first surface of the first plate external of the first region thereof is hydrophobic.

5. The device of claim 1 wherein the first region of the second plate is defined by a portion of the first surface of the second plate.

6. The device of claim 5 wherein the first region of the second plate is hydrophilic.

7. The device of claim 5 wherein the first surface of the second plate external of the first region thereof is hydrophobic.

8. The device of claim 1 wherein the first plate includes a second surface and wherein the first region of the first plate includes a recess in the second surface and a passageway extending between the recess and the first surface of the first plate.

9. The device of claim 1 wherein the first region of the second plate includes a recess in the first surface of the second plate.

10. The device of claim 1 wherein the second plate includes a second surface and wherein the magnetic force generator is a magnet positioned adjacent the second surface of the second plate for generating the magnetic force.

11. A device for isolating a target from a sample, the sample including the target bound to solid phase substrate to form target bound solid phase substrate, comprising:
    a first sample receiving region disposed on a first plate for receiving at least a portion of the sample;
    a first reagent region disposed on a second plate for receiving a reagent, the first reagent region opposing the first sample receiving region; and
    a magnetic force generator adjacent the second plate, the magnetic force generator generating a magnetic force for drawing the target bound solid phase substrate from the at least the portion of the sample, through an air gap and into the reagent when the at least the portion of the sample is received on the first sample receiving region of the first plate and when the reagent is received on the first reagent region of the second plate;
wherein:
    the first and second plates are generally parallel to and spaced from each other along an axis generally perpendicular to the first and second planes by a distance such that when the at least the portion of the sample is received on the first sample receiving region of the first plate and when the reagent is received on the first reagent region of the second plate:
        the distance between the first plate and the second plate is sufficient to provide the air gap between the at least the portion of the sample received by first sample receiving region of the first plate and the reagent received by the first reagent region of the second plate; and the target bound solid phase substrate in the at least the portion of the sample is drawn from the at least the portion of the sample, through the air gap, and into the reagent by the magnetic force generated by the magnetic force generator.

12. The device of claim 11 wherein the first plate includes a first surface, the first sample receiving region being defined by a portion of the first surface of the first plate.

13. The device of claim 12 wherein the first sample receiving region of the first plate is hydrophilic and wherein the first surface of the first plate external of the first sample receiving region thereof is hydrophobic.

14. The device of claim 12 wherein the first plate includes a second surface and wherein the first sample receiving region of the first plate includes a recess in the second surface and a passageway extending between the recess and the first surface of the first plate.

15. The device of claim 12 wherein the first reagent region of the second plate includes a recess in the first surface of the second plate.

16. The device of claim 11 wherein the second plate includes a first surface, the first reagent region being defined by a portion of the first surface of the second plate.

17. The device of claim 16 wherein the first reagent region of the first plate is hydrophilic and wherein the first surface of the second plate external of the first reagent region thereof is hydrophobic.

\* \* \* \* \*